(12) United States Patent
Mauldin

(10) Patent No.: US 8,778,026 B2
(45) Date of Patent: Jul. 15, 2014

(54) ARTIFICIAL SI JOINT

(71) Applicant: SI-Bone Inc., San Jose, CA (US)

(72) Inventor: Richard G. Mauldin, Erie, CO (US)

(73) Assignee: SI-Bone Inc., San Jose, CA (US)

( * ) Notice: Subject to any disclaimer, the term of this patent is extended or adjusted under 35 U.S.C. 154(b) by 0 days.

(21) Appl. No.: 13/791,837

(22) Filed: Mar. 8, 2013

(65) Prior Publication Data

US 2013/0245764 A1    Sep. 19, 2013

Related U.S. Application Data

(60) Provisional application No. 61/609,195, filed on Mar. 9, 2012.

(51) Int. Cl.
*A61F 2/30* (2006.01)

(52) U.S. Cl.
USPC .................. 623/17.11; 623/18.11; 606/53

(58) Field of Classification Search
USPC ................................. 623/17, 17.11
See application file for complete search history.

(56) References Cited

U.S. PATENT DOCUMENTS

| | | |
|---|---|---|
| 1,951,278 A | 3/1934 | Ericsson |
| 2,136,471 A | 11/1938 | Schneider |
| 2,243,717 A | 5/1941 | Moreira |
| 2,414,882 A | 7/1947 | Longfellow |
| 2,675,801 A | 4/1954 | Bambara et al. |
| 3,076,453 A | 2/1963 | Tronzo |
| 3,506,982 A | 4/1970 | Steffee |
| 3,694,821 A | 10/1972 | Moritz |
| 3,709,218 A | 1/1973 | Halloran |
| 4,341,206 A | 7/1982 | Perrett et al. |
| 4,344,190 A | 8/1982 | Lee et al. |
| 4,399,813 A | 8/1983 | Barber |
| 4,475,545 A | 10/1984 | Ender |
| 4,501,269 A | 2/1985 | Bagby |
| 4,569,338 A | 2/1986 | Edwards |
| 4,612,918 A | 9/1986 | Slocum |
| 4,622,959 A | 11/1986 | Marcus |
| 4,630,601 A | 12/1986 | Harder et al. |
| 4,657,550 A | 4/1987 | Daher |

(Continued)

FOREIGN PATENT DOCUMENTS

| | | |
|---|---|---|
| EP | 1287796 A1 | 3/2003 |
| JP | 05-176942 A | 7/1993 |

(Continued)

OTHER PUBLICATIONS

Mauldin et al.; U.S. Appl. No. 13/888,249 entitled "Fenestrated Implant," filed May 6, 2013.

(Continued)

*Primary Examiner* — Jerry Cumberledge
*Assistant Examiner* — Tessa Matthews
(74) *Attorney, Agent, or Firm* — Shay Glenn LLP

(57) ABSTRACT

An artificial SI-Joint includes a sacrum component and an ilium component. The sacrum component may include a ridge, foundation, perimeter surface and a fitting member. The ilium component may include a polybearing, edge, foundation, perimeter surface, and a ridge or sockets. The fitting member of the sacrum component may engage the polybearing of the ilium component to restore normal movement of the SI-Joint. The artificial SI-Joint may be implanted as a single unit or as separate pieces that are coupled together.

11 Claims, 5 Drawing Sheets

(56) References Cited

U.S. PATENT DOCUMENTS

| | | |
|---|---|---|
| 4,743,256 A | 5/1988 | Brantigan |
| 4,773,402 A | 9/1988 | Asher et al. |
| 4,787,378 A | 11/1988 | Sodhi |
| 4,790,303 A | 12/1988 | Steffee |
| 4,834,757 A | 5/1989 | Brantigan |
| 4,846,162 A | 7/1989 | Moehring |
| 4,877,019 A | 10/1989 | Vives |
| 4,878,915 A | 11/1989 | Brantigan |
| 4,904,261 A | 2/1990 | Dove et al. |
| 4,950,270 A | 8/1990 | Bowman et al. |
| 4,961,740 A | 10/1990 | Ray et al. |
| 5,034,011 A | 7/1991 | Howland |
| 5,035,697 A | 7/1991 | Frigg |
| 5,053,035 A | 10/1991 | McClaren |
| 5,066,296 A | 11/1991 | Chapman et al. |
| 5,102,414 A | 4/1992 | Kirsch |
| 5,108,397 A | 4/1992 | White |
| 5,122,141 A | 6/1992 | Simpson et al. |
| 5,139,498 A | 8/1992 | Astudillo Ley |
| 5,147,367 A | 9/1992 | Ellis |
| 5,147,402 A | 9/1992 | Bohler et al. |
| 5,190,551 A | 3/1993 | Chin et al. |
| 5,197,961 A | 3/1993 | Castle |
| 5,242,444 A | 9/1993 | MacMillan |
| 5,298,254 A | 3/1994 | Prewett et al. |
| 5,334,205 A | 8/1994 | Cain |
| 5,443,466 A | 8/1995 | Shah |
| 5,470,334 A | 11/1995 | Ross et al. |
| 5,480,402 A | 1/1996 | Kim |
| 5,569,249 A | 10/1996 | James et al. |
| 5,593,409 A | 1/1997 | Michelson |
| 5,609,636 A | 3/1997 | Kohrs et al. |
| 5,626,616 A | 5/1997 | Speece |
| 5,645,599 A | 7/1997 | Samani |
| 5,658,337 A | 8/1997 | Kohrs et al. |
| 5,667,510 A | 9/1997 | Combs |
| 5,669,909 A | 9/1997 | Zdeblick et al. |
| 5,672,178 A | 9/1997 | Petersen |
| 5,683,391 A | 11/1997 | Boyd |
| 5,713,904 A | 2/1998 | Errico et al. |
| 5,716,358 A | 2/1998 | Ochoa et al. |
| 5,743,912 A | 4/1998 | Lahille et al. |
| 5,788,699 A | 8/1998 | Bobst et al. |
| 5,800,440 A | 9/1998 | Stead |
| 5,868,749 A | 2/1999 | Reed |
| 5,928,239 A | 7/1999 | Mirza |
| 6,010,507 A | 1/2000 | Rudloff |
| 6,053,916 A | 4/2000 | Moore |
| 6,056,749 A | 5/2000 | Kuslich |
| 6,096,080 A | 8/2000 | Nicholson et al. |
| 6,120,504 A | 9/2000 | Brumback et al. |
| 6,143,031 A | 11/2000 | Knothe et al. |
| 6,210,442 B1 | 4/2001 | Wing et al. |
| 6,214,049 B1 | 4/2001 | Gayer et al. |
| 6,221,074 B1 | 4/2001 | Cole et al. |
| 6,224,607 B1 | 5/2001 | Michelson |
| 6,241,732 B1 | 6/2001 | Overaker et al. |
| 6,270,528 B1 | 8/2001 | McKay |
| 6,302,885 B1 | 10/2001 | Essiger |
| 6,302,914 B1 | 10/2001 | Michelson |
| 6,306,140 B1 | 10/2001 | Siddiqui |
| 6,319,253 B1 | 11/2001 | Ackeret et al. |
| 6,409,768 B1 | 6/2002 | Tepic et al. |
| 6,451,020 B1 | 9/2002 | Zucherman et al. |
| 6,471,707 B1 | 10/2002 | Miller et al. |
| 6,485,518 B1 | 11/2002 | Cornwall et al. |
| 6,497,707 B1 | 12/2002 | Bowman et al. |
| 6,517,541 B1 | 2/2003 | Sesic |
| 6,520,969 B2 | 2/2003 | Lambrecht et al. |
| 6,524,314 B1 | 2/2003 | Dean et al. |
| 6,565,566 B1 | 5/2003 | Wagner et al. |
| 6,575,899 B1 | 6/2003 | Foley et al. |
| 6,575,991 B1 | 6/2003 | Chesbrough et al. |
| 6,579,293 B1 | 6/2003 | Chandran |
| 6,582,431 B1 | 6/2003 | Ray |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,607,530 B1 | 8/2003 | Carl et al. |
| 6,635,059 B2 | 10/2003 | Randall et al. |
| 6,666,868 B2 | 12/2003 | Fallin |
| 6,669,529 B1 | 12/2003 | Scaries |
| 6,673,075 B2 | 1/2004 | Santilli |
| 6,692,501 B2 | 2/2004 | Michelson |
| 6,723,099 B1 | 4/2004 | Goshert |
| 6,740,118 B2 * | 5/2004 | Eisermann et al. ........ 623/17.14 |
| 6,743,257 B2 | 6/2004 | Castro |
| 7,118,579 B2 | 10/2006 | Michelson |
| 7,175,663 B1 | 2/2007 | Stone |
| 7,211,085 B2 | 5/2007 | Michelson |
| 7,223,269 B2 | 5/2007 | Chappuis |
| 7,335,205 B2 | 2/2008 | Aeschlimann et al. |
| 7,452,359 B1 | 11/2008 | Michelson |
| 7,452,369 B2 | 11/2008 | Barry |
| 7,481,831 B2 | 1/2009 | Bonutti |
| 7,534,254 B1 | 5/2009 | Michelson |
| 7,569,054 B2 | 8/2009 | Michelson |
| 7,648,509 B2 | 1/2010 | Stark |
| 7,686,805 B2 | 3/2010 | Michelson |
| 7,699,852 B2 | 4/2010 | Frankel et al. |
| 7,708,761 B2 | 5/2010 | Petersen |
| 7,758,646 B2 * | 7/2010 | Khandkar et al. ......... 623/17.15 |
| 7,850,732 B2 | 12/2010 | Heinz |
| 7,857,832 B2 | 12/2010 | Culbert et al. |
| 7,887,565 B2 | 2/2011 | Michelson |
| 7,909,832 B2 | 3/2011 | Michelson |
| 7,922,765 B2 | 4/2011 | Reiley |
| 7,942,879 B2 | 5/2011 | Christie et al. |
| 8,066,705 B2 | 11/2011 | Michelson |
| 8,066,709 B2 | 11/2011 | Michelson |
| 8,202,305 B2 | 6/2012 | Reiley |
| 8,308,779 B2 | 11/2012 | Reiley |
| 8,388,667 B2 | 3/2013 | Reiley et al. |
| 8,414,648 B2 | 4/2013 | Reiley |
| 8,425,570 B2 | 4/2013 | Reiley |
| 8,444,693 B2 | 5/2013 | Reiley |
| 8,470,004 B2 | 6/2013 | Reiley |
| 8,672,986 B2 | 3/2014 | Klaue et al. |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0038123 A1 | 3/2002 | Visotsky et al. |
| 2002/0049497 A1 | 4/2002 | Mason |
| 2002/0120275 A1 | 8/2002 | Schmieding et al. |
| 2002/0128652 A1 | 9/2002 | Ferree |
| 2002/0143335 A1 | 10/2002 | von Hoffmann et al. |
| 2002/0151903 A1 | 10/2002 | Takei et al. |
| 2002/0183858 A1 | 12/2002 | Contiliano et al. |
| 2002/0198527 A1 | 12/2002 | Mückter |
| 2003/0018336 A1 | 1/2003 | Vandewalle |
| 2003/0032961 A1 | 2/2003 | Pelo et al. |
| 2003/0065332 A1 | 4/2003 | TenHuisen et al. |
| 2003/0074000 A1 | 4/2003 | Roth et al. |
| 2003/0083688 A1 | 5/2003 | Simonson |
| 2003/0097131 A1 | 5/2003 | Schon et al. |
| 2003/0199983 A1 | 10/2003 | Michelson |
| 2003/0233147 A1 | 12/2003 | Nicholson et al. |
| 2004/0024458 A1 | 2/2004 | Senegas et al. |
| 2004/0073216 A1 | 4/2004 | Lieberman |
| 2004/0073314 A1 | 4/2004 | White et al. |
| 2004/0087948 A1 | 5/2004 | Suddaby |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0147929 A1 | 7/2004 | Biedermann et al. |
| 2004/0181282 A1 | 9/2004 | Zucherman et al. |
| 2004/0225360 A1 | 11/2004 | Malone |
| 2005/0033435 A1 | 2/2005 | Belliard et al. |
| 2005/0049590 A1 | 3/2005 | Alleyne et al. |
| 2005/0055023 A1 | 3/2005 | Sohngen et al. |
| 2005/0107878 A1 | 5/2005 | Conchy |
| 2005/0124993 A1 | 6/2005 | Chappuis |
| 2005/0137605 A1 | 6/2005 | Assell et al. |
| 2005/0159749 A1 | 7/2005 | Levy et al. |

(56) References Cited

U.S. PATENT DOCUMENTS

| | | |
|---|---|---|
| 2005/0165398 A1 | 7/2005 | Reiley |
| 2005/0228384 A1 | 10/2005 | Zucherman et al. |
| 2005/0246021 A1 | 11/2005 | Ringeisen et al. |
| 2006/0036247 A1 | 2/2006 | Michelson |
| 2006/0036251 A1 | 2/2006 | Reiley |
| 2006/0054171 A1 | 3/2006 | Dall |
| 2006/0058793 A1 | 3/2006 | Michelson |
| 2006/0084986 A1 | 4/2006 | Grinberg et al. |
| 2006/0111779 A1 | 5/2006 | Petersen |
| 2006/0129247 A1 | 6/2006 | Brown et al. |
| 2006/0161163 A1 | 7/2006 | Shino |
| 2006/0241776 A1 | 10/2006 | Brown et al. |
| 2006/0293662 A1 | 12/2006 | Boyer, II et al. |
| 2007/0083265 A1 | 4/2007 | Malone |
| 2007/0088362 A1 | 4/2007 | Bonutti et al. |
| 2007/0093841 A1 | 4/2007 | Hoogland |
| 2007/0149976 A1 | 6/2007 | Hale et al. |
| 2007/0156241 A1 | 7/2007 | Reiley et al. |
| 2007/0156246 A1 | 7/2007 | Meswania et al. |
| 2007/0161989 A1 | 7/2007 | Heinz et al. |
| 2007/0233146 A1 | 10/2007 | Henniges et al. |
| 2007/0250166 A1 | 10/2007 | McKay |
| 2007/0270879 A1 | 11/2007 | Isaza et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0065215 A1 | 3/2008 | Reiley |
| 2008/0154374 A1 | 6/2008 | Labrom |
| 2008/0161810 A1 | 7/2008 | Melkent |
| 2008/0234758 A1 | 9/2008 | Fisher et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendijk et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0306554 A1 | 12/2008 | McKinley |
| 2009/0018660 A1* | 1/2009 | Roush ................. 623/17.16 |
| 2009/0024174 A1 | 1/2009 | Stark |
| 2009/0036927 A1 | 2/2009 | Vestgaarden |
| 2009/0043393 A1* | 2/2009 | Duggal et al. ......... 623/17.16 |
| 2009/0099602 A1 | 4/2009 | Aflatoon |
| 2009/0099610 A1 | 4/2009 | Johnson et al. |
| 2009/0131986 A1 | 5/2009 | Lee et al. |
| 2009/0138053 A1 | 5/2009 | Assell et al. |
| 2009/0157119 A1 | 6/2009 | Hale |
| 2009/0163920 A1 | 6/2009 | Hochschuler et al. |
| 2009/0187247 A1 | 7/2009 | Metcalf, Jr. et al. |
| 2009/0216238 A1 | 8/2009 | Stark |
| 2009/0259261 A1 | 10/2009 | Reiley |
| 2009/0270929 A1 | 10/2009 | Suddaby |
| 2009/0287254 A1 | 11/2009 | Nayet et al. |
| 2009/0312798 A1 | 12/2009 | Varela |
| 2010/0094290 A1 | 4/2010 | Vaidya |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0145461 A1 | 6/2010 | Landry et al. |
| 2010/0191292 A1 | 7/2010 | DeMeo et al. |
| 2010/0268228 A1 | 10/2010 | Petersen |
| 2010/0280622 A1 | 11/2010 | McKinley |
| 2010/0286778 A1 | 11/2010 | Eisermann et al. |
| 2010/0331893 A1 | 12/2010 | Geist et al. |
| 2011/0009869 A1 | 1/2011 | Marino et al. |
| 2011/0022089 A1 | 1/2011 | Assell et al. |
| 2011/0040362 A1 | 2/2011 | Godara et al. |
| 2011/0046737 A1 | 2/2011 | Teisen |
| 2011/0087294 A1 | 4/2011 | Reiley |
| 2011/0118796 A1 | 5/2011 | Reiley et al. |
| 2011/0184478 A1 | 7/2011 | Reiley |
| 2011/0184518 A1 | 7/2011 | Trieu |
| 2011/0184519 A1 | 7/2011 | Trieu |
| 2011/0184520 A1 | 7/2011 | Trieu |
| 2011/0230966 A1 | 9/2011 | Trieu |
| 2011/0238181 A1 | 9/2011 | Trieu |
| 2011/0257755 A1 | 10/2011 | Bellemere et al. |
| 2011/0264229 A1 | 10/2011 | Donner |
| 2013/0053902 A1 | 2/2013 | Trudeau |
| 2013/0131739 A1 | 5/2013 | Reiley |
| 2013/0166037 A1* | 6/2013 | Goodfellow et al. ...... 623/20.32 |
| 2013/0218215 A1 | 8/2013 | Ginn et al. |
| 2013/0231746 A1 | 9/2013 | Ginn et al. |
| 2013/0245703 A1 | 9/2013 | Warren et al. |
| 2013/0253654 A1 | 9/2013 | Reiley |

FOREIGN PATENT DOCUMENTS

| | | | |
|---|---|---|---|
| JP | 2004512895 | 4/2004 | |
| JP | 2004516866 | 6/2004 | |
| WO | WO02/38054 | 5/2002 | |
| WO | WO03/007839 A2 | 1/2003 | |
| WO | WO2004/002344 | 1/2004 | |
| WO | WO2006003316 | 1/2006 | |
| WO | WO2010/105196 A1 | 9/2010 | |
| WO | WO/2011/110865 * | 9/2011 | ............... A61F 2/38 |
| WO | WO 2011/110865 A2 | 9/2011 | |

OTHER PUBLICATIONS

Reiley, Mark; U.S. Appl. No. 13/925,678 entitled "Apparatus, systems, and methods for stabilizing a spondylolisthesis" filed Jun. 24, 2013.

Al-Khayer et al.; Percutaneous sacroiliac joint arthrodesis, a novel technique; J Spinal Disord Tech; vol. 21; No. 5; pp. 359-363; Jul. 2008.

Khurana et al.; Percutaneous fusion of the sacroiliac joint with hollow modular anchorage screws, clinical and radiological outcome; J Bone Joint Surg; vol. 91-B; No. 5; pp. 627-631; May 2009.

Wise et al.; Minimally invasive sacroiliac arthrodesis, outcomes of a new technique; J Spinal Disord Tech; vol. 21; No. 8; pp. 579-584; Dec. 2008.

Reiley, Mark A.; U.S. Appl. No. 12/357,483 entitled "Systems and methods for the fixation or fusion of bone in the hand and wrist," filed Jan. 22, 2009 (abandoned).

Reiley et al.; U.S. Appl. No. 13/786,037 entitled "Systems and methods for the fixation or fusion of bone using compressive implants," filed Mar. 5, 2013.

Mauldin et al.; U.S. Appl. No. 13/791,746 entitled "Integrated implant," filed Mar. 8, 2013.

Mauldin, R. G.; U.S. Appl. No. 13/791,801 entitled "Threaded implant," filed Mar. 8, 2013.

Mauldin, R. G.; U.S. Appl. No. 13/791,849 entitled "Revision tool and method," filed Mar. 8, 2013.

Mauldin et al.; U.S. Appl. No. 13/794,542 entitled "Tissue dilator and protector," filed Mar. 11, 2013.

Mauldin et al.; U.S. Appl. No. 13/794,580 entitled "Guide pin," filed Mar. 11, 2013.

Mauldin et al.; U.S. Appl. No. 13/794,611 entitled "Impactor," filed Mar. 11, 2013.

Reiley, Mark.; U.S. Appl. No. 13/858,814 entitled "Apparatus, systems, and methods for achieving trans-iliac lumbar fusion," filed Apr. 8, 2013.

Reiley, Mark; U.S. Appl. No. 13/867,941 entitled "Apparatus, systems, and methods for achieving anterior lumbar interbody fusion," filed Apr. 22, 2013.

* cited by examiner

US 8,778,026 B2

ARTIFICIAL SI JOINT

CROSS REFERENCE TO RELATED APPLICATIONS

This patent application claims priority to U.S. Provisional Application No. 61/609,195, titled "ARTIFICIAL SI JOINT", filed on Mar. 9, 2012, which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention generally relates to an artificial sacroiliac joint prosthesis. In various respects, the invention is directed to a sacroiliac joint prosthesis for movably connecting the sacrum to the ilium.

BACKGROUND

The human hip girdle (see FIGS. 1 and 2) is made up of three large bones joined by two relatively immobile joints. One of the bones is called the sacrum and it lies at the bottom of the lumbar spine, where it connects with the L5 vertebra. The other two bones are commonly called "hip bones" and are technically referred to as the right ilium and the left ilium. The sacrum connects with both hip bones at the left and right sacroiliac joints (SI-Joint).

The SI-Joint is a diarthrodial joint and operates to transfer large mechanical loads between the low back and the legs, while simultaneously allowing enough movement for the spine and extremities to function normally during daily activities. The sacral side of the SI-Joint contains hyaline cartilage that moves against fibrocartilage on the iliac side. The joint is generally L-shaped with ridges and depressions that interlock the sacrum and the ilium. This interlocking increases friction and minimizes motion allowing the joint to have a small amount of movement.

When the joint has excessive motion, normal function of SI-Joint can be disrupted and the joint may become inflamed causing pain. The SI-Joint has been described as a pain generator for up to 22% of lower back pain. To relieve pain generated from the SI-Joint and restore normal function of the SI-Joint, surgical treatment may be indicated. For example, surgical treatment may be indicated for degenerative sacroiliitis, inflammatory sacroiliitis, iatrogenic instability of the sacroiliac joint, osteitis condensans ilii, or traumatic fracture dislocation of the pelvis. Currently, problems associated with the SI-Joint are typically treated non-surgically with medications, limiting activity, undergoing a therapy and exercise program, or radiofrequency ablation. For more serious SI-Joint problems, surgery may be performed to fuse the Si-joint, eliminating motion between the sacrum and the ilium.

There is a need for improved treatments for addressing chronic hip, joint or back pain caused by the SI-Joint.

SUMMARY OF THE DISCLOSURE

The present invention generally relates to an artificial sacroiliac joint prosthesis. In various respects, the invention is directed to a sacroiliac joint prosthesis for connecting the sacrum to the ilium and preserving motion therebetween.

Some embodiments described herein provide for an artificial SI-Joint implant for placement in a sacrum, the implant having a foundation having an outer edge, a first surface, and a second surface, the first surface opposite the second surface; a curved ridge attached to the first surface of the foundation, the curved ridge having a first end and a second end, the first and second ends located inward of the outer edge, wherein the curved ridge is configured to project from the first surface of the foundation; a fitting member attached to the second surface of the foundation, the fitting member having a concave shape configured to interface with an ilium implant.

In some embodiments, the sacrum implant has a curved ridge that is coupled to and extends from the foundation. In some embodiments, the curved ridge includes a curved cross-section. In other variations, the curved ridge includes a bell-shaped cross-section. In further embodiments, the curved ridge is configured for insertion into the sacrum.

In any of the preceding embodiments, the first surface of the foundation includes a flat surface that seamlessly meets the curved ridge. The foundation may also include a perimeter surface having an upper edge and the curved ridge is located inward of the upper edge. The perimeter surface may extend around a periphery of the foundation.

In any of the preceding embodiments, the ridge may have a first radius of curvature adapted to match a second radius of curvature for a bearing surface of the implant or another articulating implant.

In further embodiments, the implant may include a coating covering the ridge and the foundation, wherein the coating is conducive to bony in-growth. The coating may be a porous plasma spray coating. In some embodiments, the coating is formed from titanium or a titanium alloy. In other embodiments, the coating comprises a biologic aid adapted to promote bony in-growth. The biologic aid may include a growth factor. In other embodiments, the coating includes an antimicrobial agent.

In any of the preceding embodiments, the fitting member is adapted to engage a convex polybearing.

Additionally, in any of the preceding embodiments, the implant includes a proximal end, a distal end, and a length extending between the proximal and distal ends, the length being between about 20 mm to about 100 mm.

In any of the preceding embodiments, the implant has a width between about 1 cm to about 7 cm. In other embodiments, the implant has a height between about 10 mm to about 40 mm.

Additional embodiments described herein provide for an artificial SI-Joint implant for placement in an ilium having a base having an outer edge; a ridge attached to a bone-interfacing surface of the base, the ridge adapted for insertion into the ilium; and a polybearing located on a bearing surface of the base opposite the bone-interfacing surface, the bearing surface having an edge and the polybearing located inward of the edge, wherein the bearing surface is adapted to engage a sacrum implant.

In some embodiments, the polybearing has an oval shape. In other embodiments, the polybearing is formed from a thermoplastic polymer. In further embodiments, the polybearing includes a convex surface curving outward from the base.

In any of the preceding embodiments, the base includes a perimeter surface, the perimeter surface having an oval circumference.

In further embodiments, the ridge includes a curved profile. Additionally, the ridge and base may be coated with a bony in-growth promoting coating. In any of the preceding embodiments, the ridge may have a first radius of curvature adapted to match a second radius of curvature for a bearing surface of the implant.

In any of the preceding embodiments, the implant may have a proximal end, a distal end, and a length extending between the ends, the length being between about 20 mm to about 100 mm. In some embodiments, the implant may have a width between about 1 cm to about 7 cm. In any of the preceding embodiments, the implant may have a height between about 10 mm to about 40 mm.

In any of the preceding embodiments, the implant may include a mount on the base, the mount having a notch for engaging a groove in the polybearing to retain the polybearing.

Further embodiments described provide for an artificial SI-Joint including a sacrum component having a foundation with a first side and a second side, the first side coupled to a sacrum ridge and the second side coupled to a fitting member; and an ilium component having a base including a third side and a fourth side opposite the third side, the third side having a polybearing adapted for engaging the fitting member of the sacrum component to allow movement of the ilium component or sacrum component relative to the other component.

In some embodiments, the sacrum component is configured to be coupled to a sacrum bone of a patient and the ilium component is configured to be coupled to the ilium bone of the patient.

In any of the preceding embodiments, the ilium component includes an ilium ridge configured for insertion into the ilium, the ridge located on the fourth side of the ilium. In any of the preceding embodiments, the ilium ridge has a first radius of curvature adapted to match a second radius of curvature for a bearing surface of the ilium component. In any of the preceding embodiments, the ilium component comprises a socket on the fourth side of the ilium, the socket adapted to receive a screw through the ilium.

In any of the preceding embodiments, the sacrum ridge has a first radius of curvature adapted to match a second radius of curvature for a bearing surface of the sacrum component. In any of the preceding embodiments, the ridge of the sacrum component has a curved cross-section.

In any of the preceding embodiments, the polybearing is adapted to allow about 2 degrees to about 4 degrees of movement. In any of the preceding embodiments, the fitting member is configured to engage and articulate with the polybearing.

Other embodiments provide for methods of implanting an artificial SI-Joint implant. These methods include identifying an sacroiliac articulation of a patient's SI-joint; creating a first insertion path in the sacrum bone and a second insertion path the ilium bone of a patient; and inserting the implant into the first and second insertion paths in the sacrum bone and ilium bone, wherein the implant comprises a sacrum component for insertion into the sacrum bone and an ilium component for insertion into the ilium bone.

In any of the preceding embodiments, the implant is inserted along sacroiliac articulations.

In any of the preceding embodiments, the first and second insertion paths are the same. In any of the preceding embodiments, the first and second insertion paths are curved. In further embodiments, the first insertion path includes a radius of curvature corresponding to a radius of curvature for a ridge member on the sacrum component. In any of the preceding embodiments, the radius of curvature for the first insertion path is between about 10 mm to about 70 mm. In any of the preceding embodiments, the second insertion path includes a radius of curvature corresponding to a radius of curvature on a bearing surface of the ilium component. In any of the preceding embodiments, the radius of curvature for the second insertion path is between about 10 mm to about 70 mm.

In any of the preceding embodiments, the methods include unlocking the implant by removing a locking pin. In any of the preceding embodiments, the methods include rotating the implant during the inserting step.

In any of the preceding embodiments, the inserting step includes inserting a portion of the sacrum component and a portion of ilium component into the sacrum and ilium respectively.

In any of the preceding embodiments, the methods include creating a third insertion path laterally through the ilium; and inserting a screw through the third insertion path to engage a socket of the artificial SI-Joint.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Reference will now be made in detail to exemplary embodiments of the invention, examples of which are illustrated in the accompanying drawings. While the invention will be described in conjunction with the exemplary embodiments, it will be understood that they are not intended to limit the invention to those embodiments. On the contrary, the invention is intended to cover alternatives, modifications and equivalents, which may be included within the spirit and scope of the invention as described herein.

Various aspects of the present invention relate to an artificial sacroiliac joint prosthesis. In various embodiments, the artificial joint is implanted into the sacroiliac joint (SI-Joint).

Figure 1:
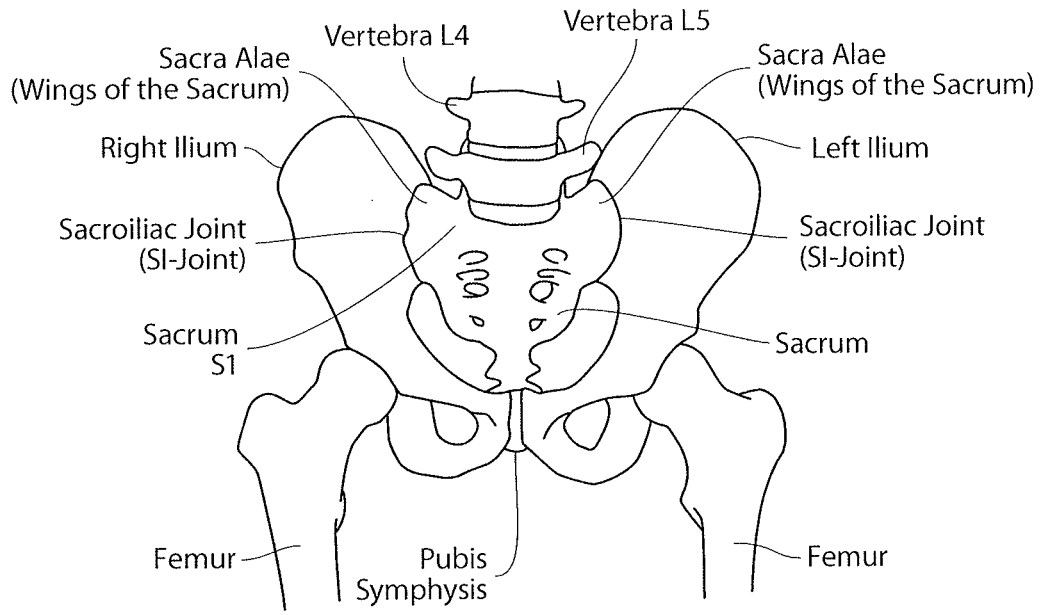
FIGS. 1-2 are, respectively, and posterior views of the human hip girdle.
Figure 2:
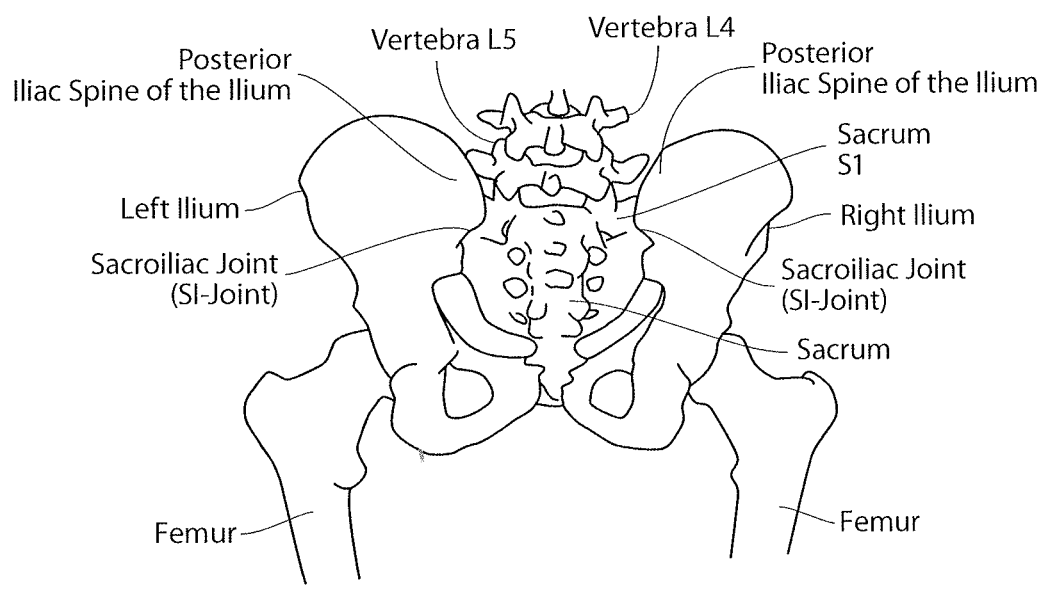

FIGS. 1-2 are, respectively, anterior and posterior views of the human hip girdle including the sacrum and the hip bones (the right ilium and the left ilium), the sacrum being connected with both hip bones at the SI-Joints.

Each joint is encased and strengthened by two main ligaments, the interosseous (not shown) and the posterior sacroiliac ligaments (not shown). The ligaments allow slight movement during non-weight bearing and less movement during weight bearing movements. The slight movement of the SI-Joint allows the joint to have enough play to provide spinal shock absorption, enhance lower extremity torque conversions and transverse rotations.

The spine and the lower extremities are connected by the pelvis. The spine movements occur in the sagittal plane and include flexion and extension. Hip movements may occur in all three planes, including a rotational motion which the lumbar spine does not perform well. As a result, the pelvic area should absorb the majority of lower extremity rotation, for example during bipedal gate.

Figure 3:
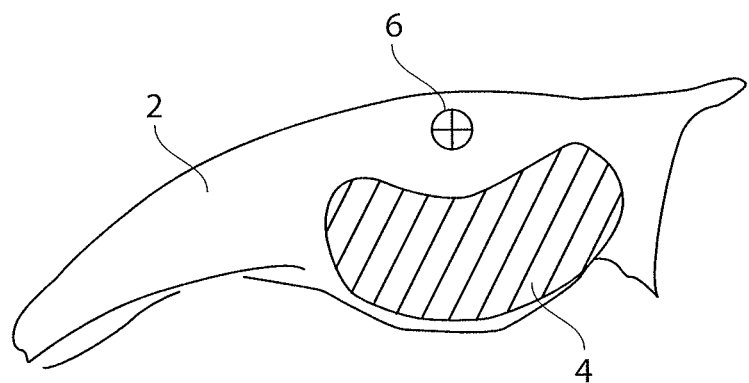
FIG. 3 is an enlarged lateral view of the sacrum.
Figure 4:
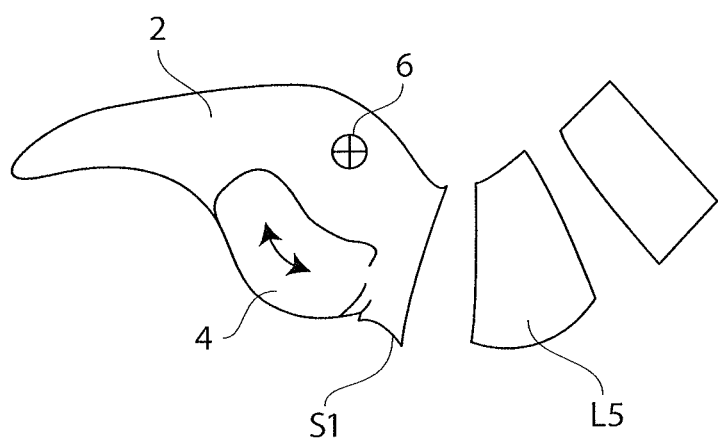
FIG. 4 is an enlarged lateral view of the sacral and lower lumbar region.

FIG. 3 is an enlarged lateral view of the sacrum. FIG. 4 is an enlarged lateral view of the sacral and lower lumbar region. The sacrum 2 includes an articular surface 4 that unites with the articular surface of the ilium (not shown). The sacroiliac articulations form the SI-Joint that is a strong synovial joint between the sacrum and the ilium. The SI-Joint contains numerous ridges and complimentary depressions that provide friction and help interlock the two bones. Additionally, the sacrum is wedged anteroposteriorly allowing it to provide resistance to vertical and horizontal translation as illustrated in FIGS. 1 and 2. Normal motion of the SI-Joint may include a combination of sliding, tilting and rotation. The SI-Joint may slide approximately 2 mm and may tilt or rotate approximately 2 to 4 degrees. The SI-Joint moves mostly along the sagittal plane about a point of rotation 6 and should not move in the transverse plane.

Figure 5:
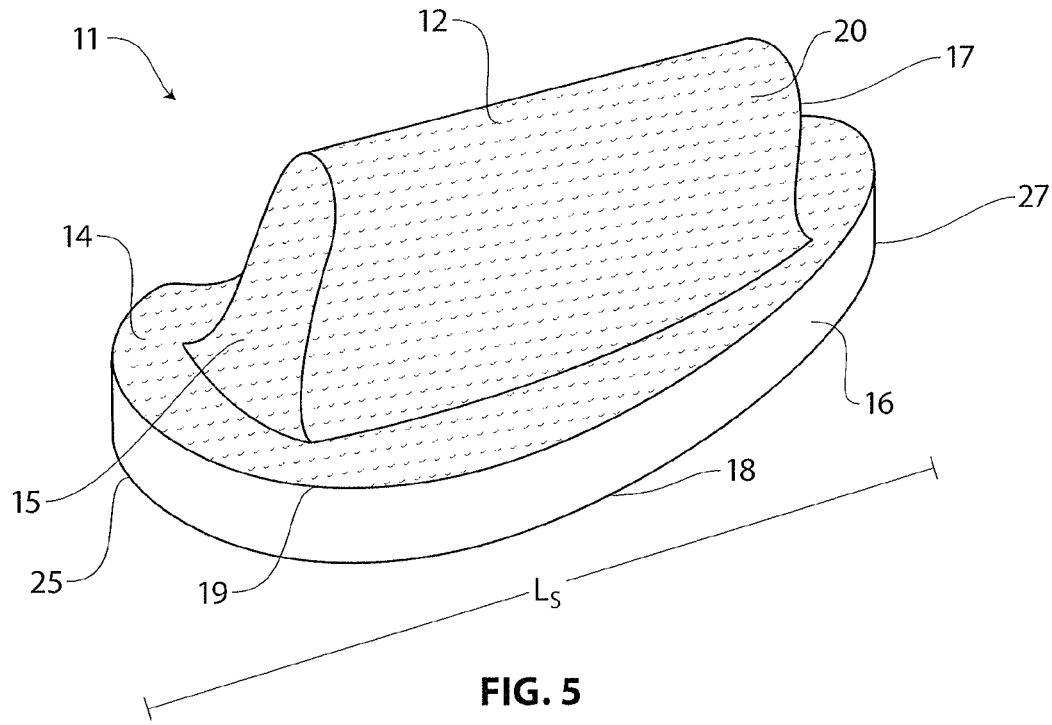
FIG. 5 is a perspective view of the sacrum component of an exemplary artificial SI-Joint.

The artificial joint may be designed to replace the SI-Joint mimicking its shape and movement. The artificial joint may include a sacrum component 11 and an ilium component 21. FIG. 5 is a perspective view of the sacrum component of an exemplary artificial SI-Joint. The sacrum component 11 may include a ridge 12, a foundation 14, a perimeter surface 16, and a fitting member 18. The ridge 12 may be coupled to and extend away from the foundation 14. In some embodiments, the ridge 12 has a generally uniform and curved cross section in the longitudinal direction. In various embodiments, ridge 12 has a bell shape cross section. Ridge 12 may include a proximal end 15 and a distal end 17. The proximal end 15 and the distal end 17 of the ridge 12 may be flat and not extend to the outer edge of foundation 14. Foundation 14 may include a generally flat surface that surrounds ridge 12. The outer edge of foundation 14 meets an upper edge 19 of perimeter surface 16. Ridge 12, foundation 14 and fitting member 18 may be formed from a polished metal or metal alloy including, but not limited to, cobalt chromium, titanium, tantalum, tivanium (aluminum, vanadium, and titanium), stainless steel or any other joint replacement metal.

Ridge 12 and foundation 14 may have a coating 20 that is conducive to bony in-growth, on-growth and/or through-growth. Coating 20 may be formed from titanium or titanium alloys. In some embodiments, the coating 20 is a porous plasma spray coating. The coating 20 may create a biomechanically rigorous artificial joint prosthesis, designed to support acute weight bearing capacity. In various embodiments, the ridge 12 and foundation 14 may be formed from a material that itself inherently possesses a structure conducive to bony in-growth, on-growth and/or through-growth, such as a porous mesh, hydroxyapatite, or other porous surface.

The coating 20 may include a material such as a biologic aid that may promote and/or enhance bony in-growth, bony on-growth, bony through-growth, tissue repair, and/or reduce inflammation, infection and pain. The biologic aid may include growth factors, such as bone morphogenetic proteins (BMPs), hydroxyapatite in a liquid or slurry carrier, demineralized bone, morselized autograft or allograft bone, medications to reduce inflammation, infection and pain such as analgesics, antibiotics and steroids. In various embodiments, the growth factors may be human recombinant growth factors, such as rh-BMP-2 and/or rh-BMP-7, or any other human recombinant form of BMP. The carrier for the biologic aid may be a liquid or gel such as saline or a collagen gel.

The biologic aid may also be encapsulated or incorporated in a controlled released formulation so that the biologic aid is released to the patient at the implant site over a longer duration. For example, the controlled release formulation may be configured to release the biologic aid over the course of days, weeks or months, and can be configured to release the biologic aid over an estimated time it would take for the implant site to heal. The amount of biologic aid delivered to the artificial SI-Joint may be controlled using a variety of techniques, such as controlling or varying the amount of coating material applied to the artificial SI-Joint and/or controlling or varying the amount of biologic aid incorporated into the coating material. Controlling the amount of biologic aid delivered may be important because excessive use of certain biologic aids may result in negative effects such as localized inflammation, local pain or radicular pain.

The coating 20 may further be covered with various other coatings such as antimicrobial, antithrombotic, and osteoinductive agents, or a combination thereof. In various embodiments, the entire artificial SI-Joint may be impregnated with such agents.

Perimeter surface 16 extends around the periphery of foundation 14. The perimeter surface 16 may be flat and form a shape that compliments the fitting member 18. In various embodiments, the perimeter surface 16 forms a circumference that is bean-shaped. In some embodiments, the perimeter surface 16 has a coating 20. Perimeter surface 16 may be formed from similar materials as that described for ridge 12 and foundation 14.

Fitting member 18 may have a concave surface and an outer edge (not shown). The concave surface may engage a convex polybearing 22 of the ilium component 21 (see FIG. 6). The outer edge of the fitting member 18 may engage an outer edge 24 of the polybearing 22.

The sacrum component 11 has a length $L_S$ that extends from the proximal end 25 to the distal end 27 of sacrum component 11. In some embodiments, the length $L_S$ may be within a range of about 20 mm to 100 mm. The length $L_S$ may be about 20 mm, 40 mm, 60 mm, 80 mm, or 100 mm.

Figure 6:
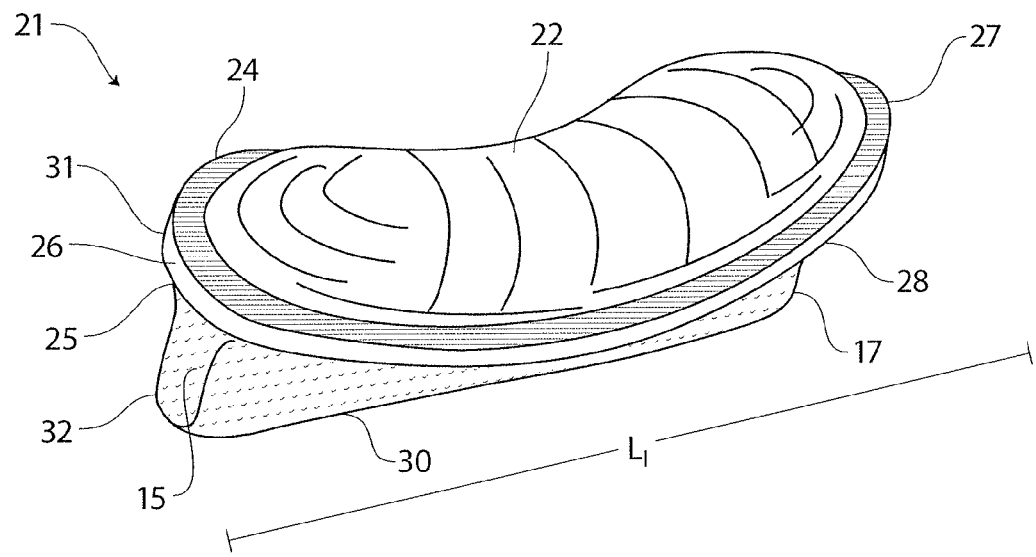
FIG. 6 is a perspective view of the ilium component of an exemplary artificial SI-Joint.

FIG. 6 is a perspective view of the ilium component of an exemplary artificial SI-Joint. The ilium component 21 may include polybearing 22, edge 24, perimeter surface 26, foundation 28, ridge 30 and coating 32. Polybearing 22 may have a bean shape. Polybearing 22 may be formed from one or more of a thermoplastic polyethylene (e.g. ultra-high molecular weight polyethylene, high-modulus polyethylene or high-performance polyethylene), organic polymer thermoplastic (e.g. polyether ether ketone), thermoset polymer, elastomer, pyrocarbon and other material. In alternative embodiments, a polybearing may be located on the sacrum component 11 (FIG. 5) while a metal or metal alloy bearing is located on the ilium component 21 (FIG. 6). In some embodiments, both the sacrum component 11 and the ilium component 21 may be made of metal or metal alloy, such as stainless steel.

The surface of polybearing 22 may be convex and may extend away from edge 24. Edge 24 may extend around the perimeter of polybearing 22. Edge 24 may have a rough or treated surface designed to increase friction when engaging a surface of fitting member 18. Edge 24 and polybearing 22 may engage a corresponding edge (not shown) and concave fitting member 18, respectively, of the sacrum component 11.

Perimeter surface 26 may extend between the edge 24 and the rim of foundation 28. The perimeter surface 26 may be flat and form a shape that is complimentary to the shape of polybearing 22. In various embodiments, the perimeter surface 26 forms a circumference that is bean shaped. Perimeter surface 26 may be formed from similar materials as those described with respect to perimeter surface 16 of the sacrum component 11.

The ridge 30 may be coupled to and extend away from the foundation 28. In some embodiments, the ridge 30 has a generally uniform and curved cross section in the longitudinal direction. In various embodiments, ridge 30 has a bell shape cross section. Ridge 30 may include a proximal end 15 and a distal end 17. The proximal end 15 and the distal end 17 of the ridge 30 may be flat and not extend to the outer edge of foundation 28. Foundation 28 may include a generally flat surface that surrounds ridge 30. The outer edge of foundation 28 meets an upper edge 31 of perimeter surface 26. Ridge 30 and foundation 28 may be formed from similar materials as those described with respect to ridge 12 and foundation 14 of the sacrum component 11. Ridge 30 and foundation 28 may have a coating 32. In some embodiments, the coating 32 may be porous. Coating 32 may be formed from similar materials as those described for coating 20 of the sacrum component 11.

The ilium component 21 has a length $L_1$ that extends from the proximal end 25 to the distal end 27 of ilium component 21. In some embodiments, the length $L_1$ may be within a range of about 20 mm to about 100 mm. The length $L_1$ may be about 20 mm, 40 mm, 60 mm, 80 mm, or 100 mm.

Figure 7:
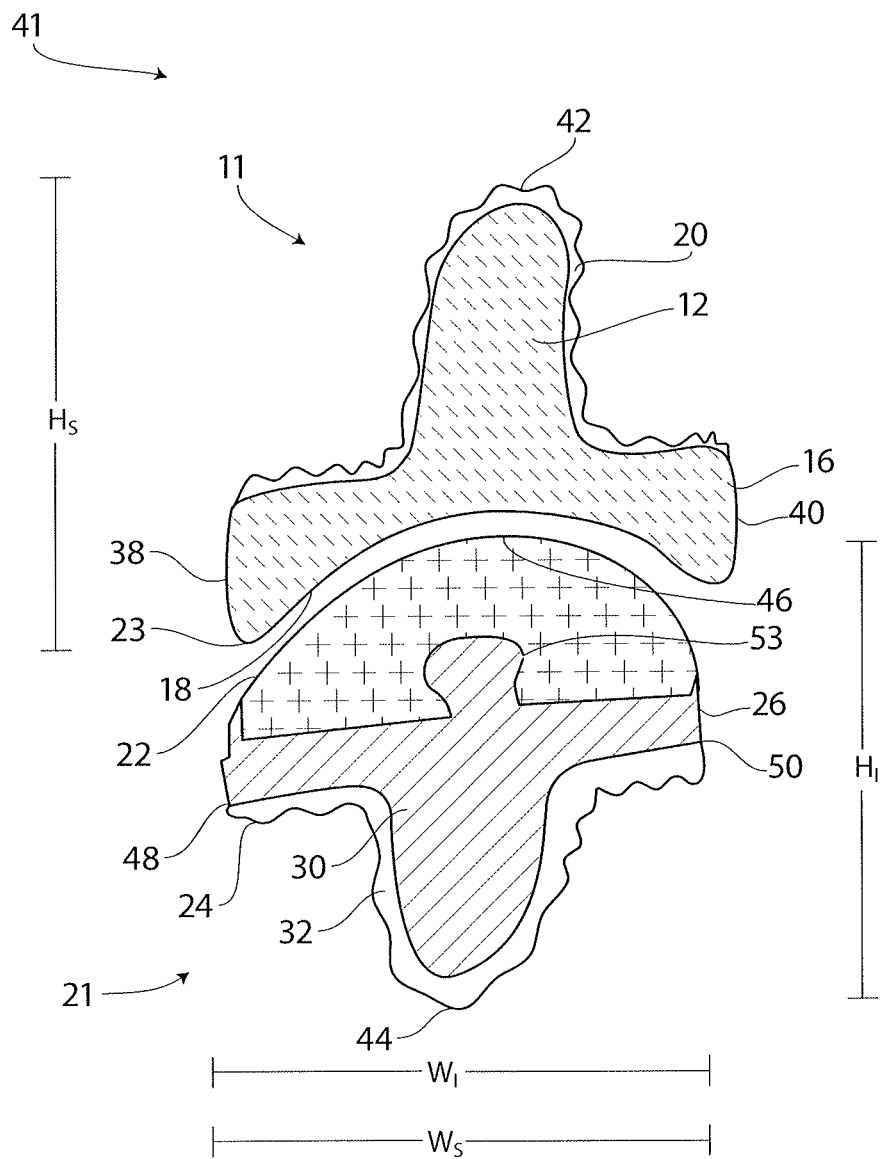
FIG. 7 is a cross-sectional view of an exemplary artificial SI-Joint.

FIG. 7 is a cross-sectional view of an exemplary artificial SI-Joint. The exemplary artificial SI-Joint 41 includes sacrum component 11 and ilium component 21. The sacrum component 11 includes ridge 12, coating 20, perimeter 16 and fitting member 18. Fitting member 18 has a concave shape that engages the convex shape of polybearing 22. The sacrum component 11 has a height $H_S$ that extends from a first point 42 on coating 20 at the top of ridge 12 to the lower edge 23 of perimeter 16. In some embodiments, the height $H_S$ may be within a range of about 10 mm to 40 mm. The height $H_S$ may be about 10 mm, 15 mm, 20 mm, 25 mm, 30 mm, 35 mm or 40 mm.

The sacrum component 11 has a width $W_S$ that extends from a first edge 38 of the perimeter surface 16 to a second edge 40 of perimeter surface 16. In some embodiments, the width of $W_S$ may be within a range of about 1 cm to 7 cm. The width $W_S$ may be about 1 cm, 2 cm, 3 cm, 4 cm, 5 cm, 6 cm or 7 cm.

The ilium component 21 includes ridge 30, coating 32, perimeter surface 26, and polybearing 22. The ilium component 21 has a height $H_I$ that extends from a first point 44 on the coating 32 of ridge 30 to a second point 46 on polybearing 22. In some embodiments, the height of $H_I$ may be within a range of about 10 mm to 40 mm. The height $H_I$ may be about 10 mm, 15 mm, 20 mm, 25 mm, 30 mm, 35 mm or 40 mm.

The ilum component 21 has a width $W_I$ that extends from a first edge 48 to a second edge 50 of the perimeter surface 26. In some embodiments, the width $W_1$ may be within a range of about 1 cm to 7 cm. The width $W_I$ may be about 1 cm, 2 cm, 3 cm, 4 cm, 5 cm, 6 cm or 7 cm. In various embodiments, $W_S$ is larger than $W_I$ to allow for rotation of the artificial SI-Joint 41. For example, $W_S$ may be 7 cm and $W_I$ may be 8 cm to allow for approximately 2 to 4 degrees of rotation.

The ilium component 21 may include a first portion and a second portion. The first portion may include ridge 30, foundation 28, perimeter surface 26, and coating 32. The second portion may include polybearing 22. The first portion may also include mount 53 that fits into a notch in polybearing 22. The cross section shape of mount 53 may form a knob and may extend in the longitudinal direction between the proximal end and distal end. The mount 53 may be formed from similar materials as described with respect to ridge 30, foundation 28, and perimeter surface 26.

Figure 8:
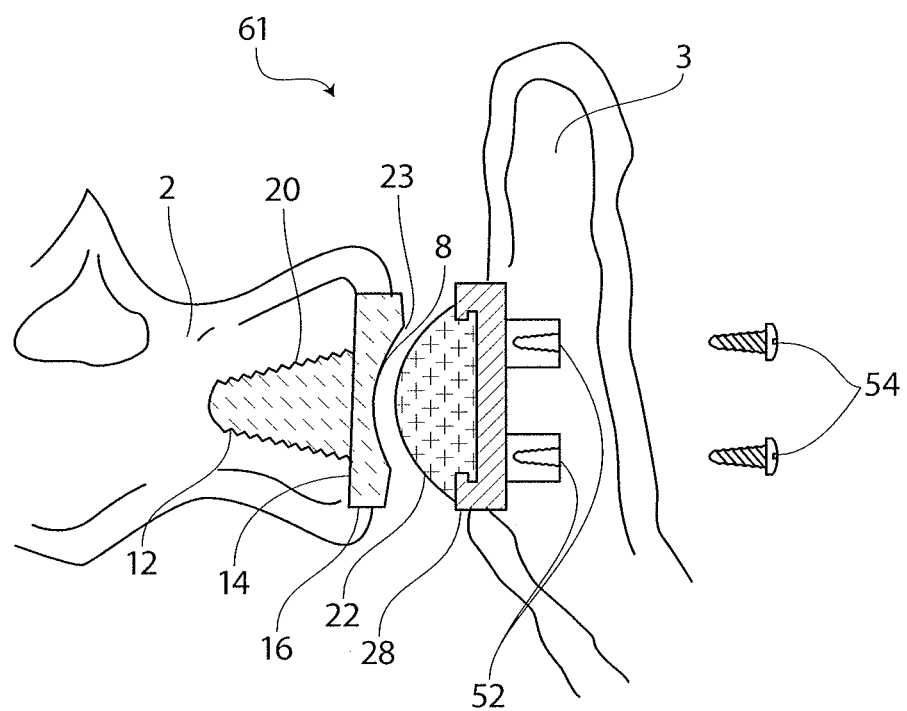
FIG. 8 is a cranio-caudal section view of an implanted exemplary artificial SI-Joint.

FIG. 8 is a cranio-caudal section view of an implanted exemplary artificial SI-Joint. The artificial SI-Joint 61 includes a sacrum component having ridge 12, foundation 14, perimeter surface 16, fitting member 18, coating 20 and edge 23. The artificial SI-Joint 61 also includes an ilium component having polybearing 22, foundation 28, and sockets 52. The polybearing 22 may engage fitting member 18 which allows movement about the sacrum 2 in the sagittal plane. The artificial SI-Joint may move in the range of about 2 to 4 degrees. Sockets 52 may receive screws 54 laterally through bone of the ilium 3. In the sacrum component, ridge 12 may be formed as a first piece and foundation 14, perimeter surface 16, and fitting member 18 may be formed as a second piece. In the ilium component, foundation 28 and sockets 52 may form a third piece and polybearing 22 may form a fourth piece.

The artificial SI-Joint like that shown in FIGS. 5-8 may be used to replace a damaged or dysfunctional SI-Joint. The artificial SI-Joint may be effectively implanted through the use of alternative surgical approaches; namely, a posterior inferior approach or a posterior superior approach. The surgical procedure is desirably aided by conventional lateral and/or anterior-posterior (A-P) visualization techniques, e.g., using X-ray image intensifiers such as a C-arms or fluoroscopes to produce a live image feed that is displayed on a TV screen.

To implant the artificial SI-joint into a patient, a physician may identify the SI-joint and the sacroiliac articulations of the SI-Joint. The artificial SI-Joint may be inserted along the surface of the sacroiliac articulations. Before insertion, the physician may identify where to place the pilot insertion path or bore through each of the sacrum bone segment and ilium bone segment. A single drill bit, multiple drill bits, reamer or other device may be employed to bore into the bone surfaces to create a pilot bore of the desired size and configuration. The physician may then insert the artificial SI-Joint into the bored portion of the sacrum 2 and ilium 3. In some embodiments, a curved insertion path or bore is formed in one or both of the sacrum and ilium, matching the radius of curvature of curved ridge(s) of the sacrum component and/or the ilium component. The radius of curvature of the ridges may be selected to match a radius of curvature of the bearing surfaces of the sacrum component and ilium component. This will allow the artificial joint to rotate about a point of rotation 6, as shown in FIG. 3. In some embodiments, the point of rotation 6 is located outside and posterior of the body (not shown.) In some embodiments, the radius of the insertion path, ridges and bearing surfaces is within the range of about 10 mm and about 70 mm. In some embodiments, it may be 100 mm. In other embodiments, the insertion path and ridges may be straight.

In some embodiments, the artificial SI-Joint may be inserted as a single unit into the SI-Joint with a locking pin. The locking pin may be removed from the artificial SI-Joint after the joint is in position. In some embodiments, the artificial SI-Joint may be inserted in pieces into the bore portions of the sacrum 2 and the ilium 3. For example, ridge 12 may first be inserted into the sacrum 2 as a first piece and foundation 14, perimeter surface 16, and fitting member 18 may then be inserted into the sacrum 2 as a second piece coupled to the first piece. Foundation 28 and sockets 52 may be inserted into the ilium as a third piece and polybearing 22 may be inserted into the ilium as a fourth piece coupled to the third piece.

Whether inserted as a single piece or multiple pieces, the artificial SI-Joint is inserted in such a manner as to avoid excessive damage to surrounding ligaments and other tissue to maximize the effectiveness of the artificial SI-Joint. When the insertion paths are curved as previously described, the artificial joint may be rotated into place as it is inserted along the path.

In an embodiment that utilizes screws 54 and sockets 52, an insertion path or bore may be formed from a lateral approach through the ilium to the sockets 52 of the artificial SI-Joint ilium component. The screws may be inserted through the ilium and received by the sockets 52 to secure the ilum component to the ilum.

The artificial SI-Joint makes possible a replacement prosthetic SI-Joint. The design and configuration of the artificial SI-Joint mimic the normal function of an SI-Joint allowing slight movement of approximately 2 to 4 degrees. A surface coating, for example a porous plasma spray coating with irregular surface, promotes bony in-growth, on-growth and/or through growth to provide a biomechanically rigorous prosthetic joint designed specifically to replace a dysfunctional SI-Joint and stabilize the heavily loaded lumbar spine. To minimize trauma to the ligaments and tissue, the artificial SI-Joint may be implanted as a single unit or as separate pieces that are coupled together.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the examples described herein, but only by the plain meaning of the claim terms employed.

What is claimed is:

1. An artificial SI-Joint implant, the implant comprising:
   a sacrum component having a foundation comprising a first side and a second side, the first side coupled to a sacrum ridge and the second side coupled to a fitting member; and
   an ilium component having a base comprising a third side and a fourth side opposite the third side, the third side having a polybearing adapted for engaging the fitting member of the sacrum component to allow movement of the ilium component or sacrum component relative to the other component, wherein the sacrum component has a first radius of curvature and the ilium component has a second radius of curvature, the first and second radius of curvatures being between about 10 mm to about 70 mm, wherein the ilium component comprises an ilium ridge configured for insertion into the ilium, the ridge located on the fourth side of the ilium component, wherein the ilium ridge has a ridge radius of curvature adapted to match a bearing radius of curvature for a bearing surface of the ilium component.

2. The implant of claim 1, wherein the sacrum component is configured to be coupled to a sacrum bone of a patient and the ilium component is configured to be coupled to the ilium bone of the patient.

3. The implant of claim 1, wherein the ilium component comprises a socket on the fourth side of the ilium component, the socket adapted to receive a screw through the ilium.

4. The implant of claim 1, wherein the polybearing is adapted to allow about 2 degrees to about 4 degrees of movement.

5. The implant of claim 1, wherein the fitting member is configured to engage and articulate with the polybearing.

6. A method of implanting an artificial SI-Joint implant, comprising:
   identifying a sacroiliac articulation of a patient's SI-joint;
   creating a first insertion path in the sacrum bone and a second insertion path in the ilium bone of a patient; and
   inserting the implant into the first and second insertion paths in the sacrum bone and ilium bone, wherein the implant comprises a sacrum component for insertion into the sacrum bone and an ilium component for insertion into the ilium bone, the first and second paths having a radius of curvature between about 10 mm to about 70 mm, wherein the sacrum component comprises a ridge having a ridge radius of curvature matching the radius of curvature for one of the first or second insertion paths.

7. The method of claim 6, wherein the implant is inserted along sacroiliac articulations.

8. The method of claim 6, wherein the ridge radius of curvature is between about 10 mm to about 70 mm.

9. The method of claim 6, further comprising creating a third insertion path laterally through the ilium; and inserting a screw through the third insertion path to engage a socket of the artificial SI-Joint implant.

10. An artificial SI-Joint implant, the implant comprising:
    a sacrum component having a foundation comprising a first side and a second side, the first side coupled to a sacrum ridge and the second side coupled to a fitting member, wherein the sacrum ridge has a ridge radius of curvature adapted to match a bearing radius of curvature for a bearing surface of the sacrum component; and
    an ilium component having a base comprising a third side and a fourth side opposite the third side, the third side having a polybearing adapted for engaging the fitting member of the sacrum component to allow movement of the ilium component or sacrum component relative to the other component, wherein the sacrum component has a first radius of curvature and the ilium component has a second radius of curvature, the first and second radius of curvatures being between about 10 mm to about 70 mm.

11. A method of implanting an artificial SI-Joint implant, comprising:
    identifying a sacroiliac articulation of a patient's SI-joint;
    creating a first insertion path in the sacrum bone and a second insertion path in the ilium bone of a patient; and
    inserting the implant into the first and second insertion paths in the sacrum bone and ilium bone, wherein the implant comprises a sacrum component for insertion into the sacrum bone and an ilium component for insertion into the ilium bone, the first and second paths having a radius of curvature between about 10 mm to about 70 mm, wherein the ilium component comprises a ridge having a ridge radius of curvature matching the radius of curvature for one of the first or second insertion paths.

\* \* \* \* \*